United States Patent [19]

Maryanoff

[11] Patent Number: 4,499,294

[45] Date of Patent: Feb. 12, 1985

[54] PROCESS FOR PRODUCTION OF METHYL 2-TETRADECYLGYCIDATE

[75] Inventor: Cynthia A. Maryanoff, New Hope, Pa.

[73] Assignee: McNeilab, Inc., Fort Washington, Pa.

[21] Appl. No.: 459,750

[22] Filed: Jan. 21, 1983

[51] Int. Cl.³ ............................................ C07D 301/02
[52] U.S. Cl. ..................................... 549/519; 549/549
[58] Field of Search ................................ 549/519, 549

[56] References Cited

U.S. PATENT DOCUMENTS

| | | | |
|---|---|---|---|
| 2,939,872 | 6/1960 | Hudson | 549/549 |
| 3,506,690 | 4/1970 | Normant et al. | 549/519 |
| 3,933,864 | 1/1976 | White | 549/519 |
| 4,196,300 | 4/1980 | Mohrbacher et al. | 549/549 |

FOREIGN PATENT DOCUMENTS 55-153777  11/1980  Japan .................................. 549/519

OTHER PUBLICATIONS

A. Weissberger, Heterocyclic Compounds with Three- and Four- Membered Rings, Part One (1964) Interscience publishers, N.Y., p. 113.

*Primary Examiner*—Norma S. Milestone
*Attorney, Agent, or Firm*—David J. Levy

[57] ABSTRACT

An improved process for producing the hypoglycemic compound, methyl 2-tetradecylglycidate, by reacting methyl α-chloropalmitate with lithium methoxide in the presence of formaldehyde in a dipolar aprotic solvent such as DMF or DMSO.

5 Claims, No Drawings

PROCESS FOR PRODUCTION OF METHYL 2-TETRADECYLGYCIDATE

This invention relates to a process for production of the known compound, methyl 2-tetradecylglycidate (II) [which could alternatively be called methyl 2-tetradecyloxiranecarboxylate], and, more particularly, to a process wherein said compound is produced as relatively high purity material in relatively high yields in a process suitable for large scale production by reacting methyl α-chloropalmitate (I) with lithium methoxide in the presence of formaldehyde.

The reaction involved in the present invention is depicted in the following Reaction Scheme (A):

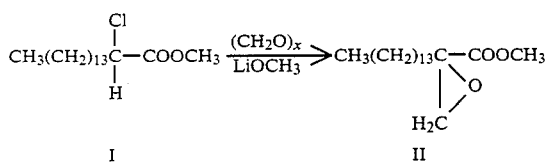

wherein $(CH_2O)_x$ refers to formaldehyde, paraformaldehyde or any other material which forms formaldehyde in situ.

BACKGROUND OF THE INVENTION

Methyl 2-tetradecylglycidate (II) is a known compound which is disclosed in Mohrbacher et al. U.S. Pat. No. 4,196,300, as itself having a pharmacologically useful hypoglycemic activity and also as being an intermediate used in making both 2-tetradecylglycidic acid and sodium 2-tetradecylglycidate dihydrate which also have pharmacologically useful hypoglycemic activities.

Thus, to make any of the aforesaid three compounds on a large scale, it is highly desirable to have a process capable of producing methyl 2-tetradecylglycidate in high yield.

DESCRIPTION OF PRIOR ART

U.S. Pat. No. 4,196,300 suggested that the Darzens glycidic ester condensation-type reaction was a general method for preparation of compounds such as II, referring to the chapter by Newman In "Organic Reactions", Vol. 5, Chapter 10, New York, John Wiley & Sons, Inc., 1949. Example XIX of said patent contains examples thereof. However, the yields obtained by the reactants and reaction conditions used were fairly low, on the order of 15 percent or less.

SUMMARY OF THE INVENTION

The present invention defines a very specific process, using the Darzens glycidic ester condensation-type reaction, which gives relatively high yields, above about 85 percent of methyl 2-tetradecylglycidate of high purity, above about 95 percent by glc. by the reaction depicted in Reaction Scheme (A) above.

DETAILED DESCRIPTION OF THE INVENTION

It was found that when an α-haloester (I) was treated with a suitable base (capable of removing an α-hydrogen) in the presence of formaldehyde, glycidic ester is formed. However, depending on reactants and reaction conditions varying amounts of dimeric products were formed as shown in the following Reaction Scheme (B):

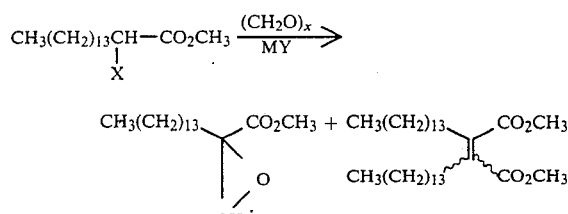

where x = Br or Cl

Thus, when the reactants and reaction conditions were: $X=Br$, $M=Na$, $(Y=OCH_3$ or $N[Si(CH_3)_3]_2)$, the major products at $-78°$ C. were dimers, while for: $X=Cl$, $M=Na(Y=OCH_3)$, the major product at $0°$ C. was methyl 2-tetradecylglycidate (II) ($\sim 80$ percent with dimeric product isolated in $\sim 20$ percent).

Using conditions which generate the most stable carbanion, in the presence of paraformaldehyde [which generates formaldehyde in situ] in DMF at room temperature, we have been able to obtain high isolated yields (85-88 percent) of methyl 2-tetradecylglycidate of high purity (96-98 percent by glc.).

Of critical importance in this process is the use of lithium methoxide as the base. The lithium methoxide may be preformed or, alternatively, generated in situ from suitable reagents such as lithium hydride and methanol. Use of other bases such as, for example, potassium carbonate, lithium carbonate, sodium methoxide, sodium hexamethyldisilazide, etc., resulted in reduced yields and impure products.

Also of importance in this process is the use of chloropalmitate ester instead of bromo or other halopalmitates. Use of the latter results in reduced yields and impure products.

It was found necessary to conduct the reaction in a particular type of solvent to obtain the high yields, namely in a dipolar aprotic solvent, in which all the reactants are soluble. Examples of such solvents include DMSO (dimethylsulfoxide) and DMF (dimethylformamide), but any other meeting the criteria may be used. The reaction may be conveniently run in a temperature range of about room temperature to about 40° C.

The following examples are intended to illustrate, but not to limit, the scope of the present invention.

EXAMPLE 1

Methyl 2-Tetradecylglycidate

Methyl α-chloropalmitate (6.1 g, 0.02 m) was dissolved in 40 ml DMF and treated with lithium methoxide (0.84, 0.022 m) followed by portionwise addition of paraformaldehyde (0.63 g, 0.021 m) over a period of about eight hours. The reaction mixture was stirred at room temperature overnight. The reaction was worked up by neutralization to pH 7 with methanol-HCl, evaporation of the DMF; the residue was dissolved in ether and filtered. Evaporation of the ether led to 99.5 percent recovery of methyl 2-tetradecylglycidate as an oil. Crystallization from methanol (twice) gave material with a melting point of 40°-42°.

EXAMPLE 2

Methyl 2-tetradecylglycidate

Methyl α-chloropalmitate (61 g, 0.20 m) was dissolved in 400 ml DMF and treated with lithium methoxide (8.35 g, 0.22 m) followed by portionwise addition of paraformaldehyde (6.3 g, 0.21 m) over a period of about eight hours. The reaction was stirred overnight, 12 hours after complete addition, at room temperature. It was worked up by extraction with hexane; the hexane was dried and evaporated to yield 53 g (89 percent) methyl 2-tetradecylglycidate (97 percent purity by glc) with m.p. 45°–48° C. after recrystallization from methanol.

EXAMPLE 3

Methyl 2-Tetradecylglycidate

A suspension of lithium methoxide (0.41 g, 0.011 m) in 10 ml of dry DMSO was treated with a suspension of methyl α-chloropalmitate (3.05 g, 0.010 m) in 10 ml of dry DMSO at 35° C., then with paraformaldehyde (0.300 g, 0.01 m) added portionwise over 8½ hours. The reaction mixture was stirred at 35° C. for an additional two hours then overnight at room temperature. It was extracted with hexane. Water was added to the DMSO layer and this was extracted twice with hexane. The combined hexane extracts were washed with water, dried and evaporated to a clear oil which crystallized (2.49 g, 84%). Glc analysis of product showed 97.5 percent methyl 2-tetradecylglycidate.

EXAMPLE 4

Methyl 2-Tetradecylglycidate

Lithium hydride (0.32 g, 0.040 m), paraformaldehyde (0.16 g, 0.0053 m), and methanol (0.32 g, 0.010 m) were heated together in 25 ml DMF at 30°–40° C. After 1 hour, methyl α-chloropalmitate (3.05 g, 0.010 m) was added; the remaining paraformaldehyde (0.16 g, 0.0053 m) was added in two portions. The reaction was worked up after 5½ hours of heating. The reaction mixture was extracted with hexane; the hexane was washed with water and dried over $Na_2SO_4$. The mixture was filtered and stripped to a crystalline residue. The residue was recrystallized from methanol to give 2.49 g (83.5%) yield of methyl tetradecylglycidate (m.p. 47°–48° C., glc purity > 99%).

I claim:

1. A process for producing methyl 2-tetradecylglycidate by reacting methyl α-chloropalmitate with lithium methoxide in the presence of formaldehyde in a dipolar aprotic solvent in which all the above reactants are soluble.

2. The process of claim 1 wherein the solvent is dimethylformamide.

3. The process of claim 1 wherein the solvent is dimethylsulfoxide.

4. The process of claim 1, wherein the formaldehyde is supplied in the form of paraformaldehyde.

5. The process of claim 1, wherein the lithium methoxide is generated in situ from lithium hydride and methanol.

* * * * *